United States Patent [19]
DiCosimo et al.

[11] Patent Number: 4,876,348
[45] Date of Patent: Oct. 24, 1989

[54] PROCESS FOR MAKING 3-CYANOPYRIDINE

[75] Inventors: Robert DiCosimo, Shaker Heights; James D. Burrington, Richmond Heights; Dev D. Suresh, Macedonia, all of Ohio

[73] Assignee: The Standard Oil Company, Cleveland, Ohio

[21] Appl. No.: 792,421

[22] Filed: Oct. 29, 1985

[51] Int. Cl.$^4$ ............... C07D 213/57; C07D 213/133
[52] U.S. Cl. .................... 546/252; 546/250; 546/251; 546/286
[58] Field of Search ............... 546/286, 250, 252, 251

[56] References Cited

U.S. PATENT DOCUMENTS

| | | | |
|---|---|---|---|
| 3,180,871 | 4/1965 | Hargrave | 546/252 |
| 4,482,719 | 11/1984 | Beschke et al. | 546/286 |
| 4,521,602 | 6/1985 | Rebafka et al. | 546/184 |
| 4,603,207 | 7/1986 | Di Cosimo et al. | 546/286 |

FOREIGN PATENT DOCUMENTS

| | | | |
|---|---|---|---|
| 1164437 | 3/1984 | Canada | 546/286 |
| 1169864 | 6/1984 | Canada | 546/286 |

*Primary Examiner*—Alan L. Rodman
*Attorney, Agent, or Firm*—C. S. Lynch; D. J. Untener; L. W. Evans

[57] ABSTRACT

Disclosed is a process comprising (1) dehydrocyclization of 2-methylglutaronitrile over Pt or Pd based catalysts to make a mixture containing 3-methylpyridine and lesser amounts of 3-methylpiperidine and (2) reacting such a mixture with $NH_3$ and $O_2$ over certain oxide catalysts containing P, V and Mo to obtain 3-cyanopyridine.

6 Claims, No Drawings

PROCESS FOR MAKING 3-CYANOPYRIDINE

This invention relates to a process for making 3-cyanopyridine from 2-methylglutaronitrile by an economical 2-step process.

2-methylglutaronitrile is industrially available in large quantities at low prices, as a by-product obtained in the process for making hexamethylene diamine from 1,3-butadiene and HCN. The composition of this available stream varies, but in addition to 2-methylglutaronitrile, it contains small amounts of impurities, viz., 2-ethylsuccinonitrile (the main impurity) cresol, benzonitrile and adiponitrile.

The dehydrocyclization reaction of 2-methylglutaronitrile is illustrated in European patent applications 82-100,681.4 (Publication No. 57,890, published Aug. 18, 1982) and 82-102,584.8 (Publication No. 62,264, published Mar. 31, 1981). In these applications it will be seen that a mixture of 3-methylpyridine with smaller amounts of 3-methylpiperidine is produced.

It is well known in general to ammoxidize 3-methylpyridine to 3-cyanopyridine. For instance, see U.S. Pat. No. 4,001,255 using a vanadium oxide catalyst. It is also known to react 3-methylpiperidine with molecular oxygen and ammonia. In U.S. Pat. No. 3,555,021 about a 50 percent yield of 3-cyanopyridine is produced in such a reaction using a cobalt molybdate catalyst.

We have ammoxidized 3-methylpyridine with ammonia and molecular oxygen at very high yields and selectivities to 3-cyanopyridines using certain catalysts containing P, V, Mo and oxygen. Attempts to react 3-methylpiperidines with ammonia and molecular oxygen led to only low yields of 3-cyanopyridines using these same catalysts. This is illustrated in Examples 6 and 7 herein.

It is an object of the present invention to provide an economic process for making 3-cyanopyridine.

Other objects, as well as features, aspects and advantages of the invention will become apparent from a study of the specification, including the examples and the claims.

This and other objects are realized by the present invention according to which there is provided a process for making 3-cyanopyridine which comprises the following steps:

(1) reacting 2-methylglutaronitrile in a known reaction by heating said nitrile in the vapor phase in admixture with 5-50 moles of hydrogen gas while in contact with a Pt or Pd catalyst to produce a mixture containing 3-methylpyridine and lesser amounts of 3-methylpiperidine wherein the molar ratio of the former to the latter is at least 3:1, (2) separating the normally liquid effluent from step (1) from the gaseous components of the effluent, and (3) reacting in a reaction zone normally liquid effluent containing 3-methylpyridine and 3-methylpiperidine, together with NH$_3$ and molecular oxygen, while in vapor phase contact with a solid catalyst which is a complex oxide having the elements and the amounts thereof indicated by the empirical formula $$P_a V_b Mo_c M_d O_x$$

wherein
M is one or any number more of Sb, Fe, W, Cu, K, Cs, B, Te, Sn, Mn, Nb, U, bi and Cr, and
a = 1.0–3,
b = 0.1–6,
a+b = at least 1.5,
c = 12,
d = 0–4, and
x is a number sufficient to satisfy the valence requirements of other elements present, under the reaction conditions suitable for ammoxidizing 3-methylpyridine over such catalysts, wherein the feed initially contacting the catalyst in said reaction zone contains a molar ratio of 3-methylpyridine to 3-methylpiperidine of at least 3:1.

We have found that we can not only react NH$_3$ and oxygen with 3-methylpiperidine, simultaneously with 3-methylpyridine, over the same catalyst, but also that the yield of 3-cyanopyridine from 3-methylpiperidine is greatly enhanced when the reaction is effected while in admixture with 3-methylpyridine. This enables us to use the liquid product mixture, obtained from the reaction of 2-methylglutaronitrile discussed above, as feed to the reaction step with ammonia and molecular oxygen. The overall process is therefore advantageous and economical.

In the catalysts of the formula discussed above, usually a is 0.2–3 and b is 0.5–4.

The catalysts of the formula noted above can optionally be mixed with or deposited on a support such as silica, silica-alumina, alumina, zirconia, titanium dioxide and the like. The active catalyst can be 1–100 percent of the solid catalyst.

In the second step, air is a convenient source of molecular oxygen, although oxygen per se can be used, or air that is diluted with additional nitrogen.

While such suitable reaction conditions are not the heart of the present invention, the usual reaction conditions are 350°–460° C., more usually 365°–420° C.; pressure 0.8 to 1.5 atmospheres, although higher or lower pressures can be used; contact time 0.1 to 20 seconds, usually 0.5 to 10 seconds; and molar feed ratios per mole of combined heterocyclic substrate, 3–12, usually 4–10, NH$_3$; 2.5–7, usually 3–5, molecular oxygen. Suitable catalyst reactor types include a fixed bed reactor or a reactor in which a solid bed of particulate catalyst flows downwardly countercurrent to the feed gases.

Normally, the catalysts of the above formula are prepared by mixing the catalyst ingredients in the proper proportions in an aqueous mixture, drying the resulting aqueous slurry and calcining the product. The ingredients going into the preparation of the catalysts can be oxides, halides, nitrates, acetates, or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 250° C. and 600° C. This calcination can take place outside of the catalytic reactor or an in situ activation can be utilized.

The invention is illustrated by the following examples, which are not to be considered as limiting. In Example 3 the 2-methylglutaronitrile fed to the reaction tube contained the impurities mentioned hereinbefore in the amount of about 20 weight percent. In other words each mole of the 2-methylglutaronitrile amount listed in that example was accompanied by 0.25 moles of such impurities.

EXAMPLE 1

A catalyst was made as follows:

| Ingredients used | Grams |
| --- | --- |
| $PdCl_2$ | 4.17 |
| Silica sol (Nalco 2327, 40% $SiO_2$) | 43.75 |
| Alumina sol (Nyasol A9235, 21% $Al_2O_3$) | 23.81 |

The $PdCl_2$ was suspended in ~20 cc $H_2O$ then added to the silica sol with constant stirring. The alumina sol was then added and the mixture jelled within 1-2 minutes. It was put into the drying oven at 120° C., where it liquified again. It was then evaporated on a hot plate with constant stirring until the volume had decreased considerably and the mixture jelled again. It was then dried at 120° C. Then the catalyst was denitrified by heating at 290° C. for 3 hours, then heating up to 425° C. over a 2 hour period, at which temperature it was held for 3 hours. Thereafter the catalyst was ground to 20-35 mesh size. The ground catalyst was heated for 6 hours at 450° C.

EXAMPLE 2

Into a 1 L beaker containing 400 mL of distilled $H_2O$ was added 11.7 g (0.100 mol) of $NH_4VO_3$ and the resulting mixture heated to 80° C. with stirring. To this mixture was added 3.8 g (0.33 mol) of 85 percent $H_3PO_4$, and the mixture turned from a cloudy white suspension to a clear red solution. This solution was added at 80° C. with stirring to a mixture of 70.6 g (0.57 mol) of $(NH_4)_6Mo_7O_{24}.4H_2O$ in 250 mL of distilled $H_2O$ also at 80° C. To the resulting clear red solution was added 43.0 g of Nalco 2327 silica sol (40 percent $SiO_2$), and the resulting mixture boiled down to ca. 200 mL with vigorous stirring. When mixture could no longer be stirred, it was heated at 120° C. for 16 hours, 290° C. for 3.0 hours, 425° C. for 16 hours, and finally at 540° C. for 4.0 hours, and the resulting brown solid ground and screened to 20-35 mesh. This catalyst has the empirical formula 80%$PV_3Mo_{12}O_x$.20%$SiO_2$. The $SiO_2$ is of course the support.

EXAMPLE 3

A glass tube 5/16 inch ID was packed with 2 cc of the catalyst of Example 1. Hydrogen and vaporized 2-methylglutaronitrile was fed into the reaction tube in the ratio of 48 moles of $H_2$ for each mole of 2-methylglutaronitrile. The tube was held at about 280° C., and the $H_2$-MGN mixture was fed at a rate such that the contact time was 2.4 seconds. After 20 hours, product was collected for one hour, while separating the gaseous products. Analysis of the liquid products by gas chromatography using a split-list capillary injection column showed that conversion was 100 percent, and yields were 70.1 percent 3-methylpyridine and 15.4 percent 3-methylpiperidine, ratio of 82 moles 3-methylpyridine to 18 moles of 3-methylpiperidine.

The following ammoxidation runs were performed in a 5 cc tubular steel microreactor equilibrated in a salt bath at the desired reaction temperature. The catalyst was placed in the microreactor tube between 2 layers of pyrex glass wool. The organic substrate was fed by syringe using an Orion Research Sage Pump. Air and ammonia flow rates were controlled by either a Brooks Dual-Channel or a Tylan Mass Flow Controller.

EXAMPLE 4

2.0 cc of the 80% $PV_3MO_{12}O_x$.20% $SiO_2$ catalyst of Example 2 was placed in the microreactor and equilibrated at 405° C., then a gaseous mixture containing 7.5 moles of $NH_3$ and 19.9 moles of air for each mole of the mixed heterocyclic containing 0.82 mole of 3-methylpyridine and 0.18 mole of 3-methylpiperidine was fed through the reactor using a contact time of 6.4 seconds. Conversion of the methylpiperidine was 100 percent and conversion of the methylpyridine was 92 percent. For each mole of combined 3-methylpiperidine plus 3-methylpyridine fed was obtained 0.853 mole of 3-cyanopyridine. If it be assumed that all of the converted 3-methylpyridine formed 3-cyanopyridine, the minimum selectivity of 3-methylpiperidine to 3-cyanopyridine was 50 percent.

In this and all other examples of this reaction the amounts of heterocyclic nitrile and 3-methylpyridine products and of unreacted substrate were determined by collecting the reactor effluent in a scrubber containing 10 ml of toluene at 0° C., and analyzing the resulting solution by g.c. on a 30-meter×0.32 mm ID capillary BP-10 column, using undecane as internal standard.

EXAMPLE 5

2.0 cc of 80% $PV_3MO_{12}O_x$.20%$SiO_2$ catalyst of Example 2 was placed in the microreactor and equilibrated at 405° C., then a gaseous mixture of 0.83 methylpyridine: 0.17 3-methylpiperidine: 8 $NH_3$: 21.5 air was fed through the reactor using a contact time of 6.4 seconds. Data taken after 162 hours showed that conversion of the 3-methylpiperidine was 100 percent and conversion of the 3-methylpyridine was 95.5 percent. For each mole of combined 3-methylpiperidine plus 3-methylpyridine fed there was obtained 0.89 mole of 3-cyanopyridine. If it be assumed that all of the converted 3-methylpyridine formed 3-cyanopyridine, the minimum selectivity of 3-methylpiperidine to 3-cyanopyridine was 57 percent.

Examples 6 and 7 illustrate the low conversion to 3-cyanopyridine obtained when reacting 3-methylpiperidine with molecular oxygen and ammonia without 3-methylpyridine in the feed.

EXAMPLE 6

2.0 cc of 80% $PV_3Mo_{12}O_x$.20%$SiO_2$ catalyst of Example 2 was placed in the microreactor and equilibrated at 405° C., then a gaseous mixture of 1.0 3-methylpiperidine: 7.5 $NH_3$: 19.9 air (mole ratios) were fed through the reactor using a contact time of 4.0 seconds. After 5 hours on stream the conversion of the substrate was 100 percent, selectivity to 3-cyanopyridine was 6.4 percent and selectivity to 3-methylpyridine was 52.8 percent.

EXAMPLE 7

2.0 cc of 80% $PV_3MO_{12}O_x$.20% $SiO_2$ catalyst of Example 2 was placed in the microreactor and equilibrated at 405° C., then a gaseous mixture of 1.0 3-methylpiperidine: 4.3 $NH_3$: 13.1 air was fed through the reactor using a contact time of 4.5 seconds. The conversion of the substrate was 100 percent, selectivity to 3-cyanopyridine was 15.1 percent and selectivity to 3-methylpyridine was 58.2 percent.

EXAMPLE 8

2.0 cc of 80% $PV_3Mo_{12}O_x$·20% $SiO_2$ catalyst of Example 2 was placed in the microreactor and equilibrated at b 405° C., then a gaseous mixture of 0.465 3-methylpyridine: 0.535 3-methylpiperidine: 7.2 $NH_3$: 19.1 air was fed through the reactor using a contact time of 4 seconds. Conversion of the 3-methylpiperidine plus 3-methylpiperidine was only 57.3 percent. The yield of 3-cyanopyridine based on the combined feeds was only 35.3 percent, with a selectivity of 61.6 percent. This example, outside the invention, shows that the advantages of the invention are not obtained when the feed contains too much 3-methylpiperidine.

As will be evident to those skilled in the art various modifications of this invention can be made or followed in the light of the foregoing disclosure and discussion without departing from the spirit and scope of the disclosure or from the scope of the claims.

We claim:

1. A process for making 3-cyanopyridine which comprises the following steps:
   (1) reacting 2-methylglutaronitrile in a known reaction by heating said nitrile in the vapor phase in admixture with 5–50 moles of hydrogen gas while in contact with a Pt or Pd catalyst to produce a mixture containing 3-methylpyridine and lesser amounts of 3-methylpiperidine wherein the molar ratio of the former to the latter is at least 3:1,
   (2) separating the normally liquid effluent from step (1) from the gaseous components of the effluent,
   (3) reacting in a reaction zone normally liquid effluent from step 1 containing 3-methylpyridine and 3-methylpiperidine, together with $NH_3$ and molecular oxygen, while in vapor phase contact with a solid catalyst which is a complex oxide having the elements and the amounts thereof indicated by the empirical formula $$P_aV_bMo_cM_dO_x$$

wherein
M is one or any number more of Sb, Fe, W, Cu, K, Cs, B, Te, Sn, Mn, Nb, U, Bi and Cr and
a=0.1–3,
b=0.1–6,
a+b=at least 1.5,
c=12,
d=0–4, and
x is a number sufficient to satisfy the valence requirements of other elements present, under the reaction conditions suitable for ammoxidizing 3-methylpyridine over such catalyst, wherein the feed initially contacting the catalyst in said reaction zone contains a molar ratio of 3-methylpyridine to 3-methylpiperidine of at least 3:1, thereby producing said 3-cyanopyridine.

2. A process according to claim 1 wherein a is 0.2–3 and b is 0.54.

3. A process according to claim 1 wherein the molar ratio of 3-methylpyridine to 3-methylpiperidine is at least 4:1.

4. A process for making 3-cyanopyridine which comprises the following steps:
   (1) reacting 2-methylglutaronitrile in a known reaction by heating said nitrile in the vapor phase in admixture with 5–50 moles of hydrogen gas while in contact with a Pt or Pd catalyst to produce a mixture containing 3-methylpyridine and lesser amounts of 3-methylpiperidine wherein the molar ratio of the former to the latter is at least 3:1,
   (2) separating the normally liquid effluent from step (1) from the gaseous components of the effluent, and
   (3) reacting in a reaction zone normally liquid effluent from Step 1 containing 3-methylpyridine and 3-methylpiperidine, together with $NH_3$ and molecular oxygen, while in vapor phase contact with a solid catalyst which is a complex oxide having the elements and the amounts thereof indicated by the empirical formula $$P_aV_bMo_cM_dO_x$$

wherein
M is one or any number more of Sb, Fe, W, Cu, K, Cs, B, Te, Sn, Mn, Nb, U, Bi and Cr and
a=0.1–3,
b=0.1–6,
a+b=at least 1.5,
c=12,
d=0–4, and
x is a number sufficient to satisfy the valence requirements of other elements present, under the reaction conditions suitable for ammoxidizing 3-methylpyridine over such catalyst, wherein the feed initially contacting the catalyst in said reaction zone contains a molar ratio of 3-methylpyridine to 3-methylpiperidine of at least 3:1, and wherein the mole ratios in the feed to the reaction zone of (3-methylpyridine+3-methylpiperidine): $NH_3$: molecular oxygen are in the range 1:3–12:2.5–7, thereby producing said 3-cyanopyridine.

5. A process of claim 4 wherein the mole ratios in the feed to the reaction zone of (3-methylpyridine+3-methylpiperidine): $NH_3$: molecular oxygen are in the range of 1:4–10:3–5.

6. A process according to claim 4 wherein the molar ratio of 3-methylpyridine to 3-methylpiperidine is at least 4:1.

* * * * *